US008178103B2

(12) United States Patent
Hesse

(10) Patent No.: US 8,178,103 B2
(45) Date of Patent: May 15, 2012

(54) PORCINE REPRODUCTIVE AND RESPIRATORY SYNDROME VIRUS STRAINS AND COMPOSITIONS

(75) Inventor: Richard A. Hesse, Manhattan, KS (US)

(73) Assignee: Intervet International B.V., Boxmeer (NL)

( * ) Notice: Subject to any disclaimer, the term of this patent is extended or adjusted under 35 U.S.C. 154(b) by 439 days.

(21) Appl. No.: 11/719,715

(22) PCT Filed: Nov. 9, 2005

(86) PCT No.: PCT/US2005/040366
§ 371 (c)(1),
(2), (4) Date: Mar. 31, 2009

(87) PCT Pub. No.: WO2006/055331
PCT Pub. Date: May 26, 2006

(65) Prior Publication Data
US 2009/0238844 A1    Sep. 24, 2009

Related U.S. Application Data

(60) Provisional application No. 60/629,873, filed on Nov. 19, 2004, provisional application No. 60/674,002, filed on Apr. 21, 2005.

(51) Int. Cl.
*A61K 39/12*    (2006.01)

(52) U.S. Cl. .......................................... 424/186.1; 435/5

(58) Field of Classification Search ........................ None
See application file for complete search history.

(56) References Cited

U.S. PATENT DOCUMENTS 5,976,537 A  *  11/1999  Mengeling et al. ........ 424/184.1

FOREIGN PATENT DOCUMENTS

| | | |
|---|---|---|
| EP | 0676467 A2 | 7/1995 |
| EP | 0835929 A1 | 4/1998 |
| EP | 0835930 A1 | 4/1998 |
| EP | 1350840 A1 | 8/2003 |
| WO | 0065032 | 11/2000 |
| WO | 0207802 A1 | 1/2002 |

OTHER PUBLICATIONS

Allende, R. et al. Mutations in the genome of porcine reproductive and respiratory syndrome virus responsible for the attenuation phenotype. Archives of Virology, 2000, 145:1149-1161.

Storgaard, T. et al. Examination of the selective pressures on a live PRRS vaccine virus. Archives of Virology, 1999, 144:2389-2401.

Done, S.H., et al., "Porcine Reproductive and Respiratory Syndrome (PRRS): A Review, with Emphasis on Pathological, Virological and Diagnostic Aspects", Br. Vet. J., 152(2):153-174 (1996).

Meng, Xiang-Jin, et al., "Sequence Comparison of Open Reading Frames 2 to 5 of Low and High Virulence United States Isolates of Porcine Reproductive and Respiratory Syndrome Virus", Journal of General Virology, 76:3181-3188 (1995).

Wesley, Ronald D., et al., "Differentiation of a Porcine Reproductive and Respiratory Syndrome Virus Vaccine Strain from North American Field Strains by Restriction Fragment Length Polymorphism Analysis of ORF 5", Journal of Veterinary Diagnostic Investigation, 10:140-144 (1998).

Gorcyca et al., "RespPRRS: A New Tool for the Prevention And Control of PRRS in Pigs", Proceedings of the American Association of Swine Practitioners 26th Annual Meeting, Omaha, Nebraska, Mar. 4-7, 1995, pp. 1-22.

Hesse et al., "Efficacy of Prime Pac PRRS in Controlling PRRS Reproductive Disease: Homologous Challenge", Proceedings of the American Association of Swine Practitioners, 1996, pp. 103-110.

* cited by examiner

*Primary Examiner* — Ali R. Salimi
(74) *Attorney, Agent, or Firm* — William M. Blackstone

(57) ABSTRACT

This invention relates to two attenuated strains of porcine reproductive and respiratory syndrome virus (PRRSV) and immunogenic compositions comprising one or more strains of attenuated porcine reproductive and respiratory syndrome virus (PRRSV).

12 Claims, No Drawings

SEQUENCE LISTING

<160> NUMBER OF SEQ ID NOS: 2

<210> SEQ ID NO 1
<211> LENGTH: 603
<212> TYPE: DNA
<213> ORGANISM: Porcine reproductive and respiratory syndrome virus

<400> SEQUENCE: 1

```
atgttgggga aatgcttgac cgcgggctat tgctcgcgat tgctttcttt gtggtgtatc      60
gtgccgttct gttttgctgt gctcgtcaac gccaacaaca gcagcagctc tcattttcag    120
tcgatttata acttgacgct atgtgagctg aatggcacag attggctggc ttcatccttc    180
aattgggcag tggagacttt tgttgttttt cccgtgttga ctcatattgt ttcctacggt    240
gcacttacca ccagccattt ccttgacaca gttggtctgg tcactgtgtc caccgccggg    300
ttttatcacg gcggtacgt cttgagtagc atctacgcgg tctgtgccct ggctgcgttg    360
atttgcttcg tcattagatt tgcgaagaac tgcatgtctt ggcgctactc atgtaccaga    420
tataccaact tccttctaga tactaagggc agactctatc gttggcggtc gcctgttatc    480
atagagaaag ggggtaaggt tgaggtcgaa ggccacctga tcgatctcaa aagagttgtg    540
cttgatggtt ccgtggcaac tcctttaacc agagtttcag ctgaacaatg gggtcgtccc    600
tag                                                                  603
```

<210> SEQ ID NO 2
<211> LENGTH: 603
<212> TYPE: DNA
<213> ORGANISM: Porcine reproductive and respiratory syndrome virus

<400> SEQUENCE: 2

```
atgttgggga aatgcttgac cgcgggctgt tgctcgcaat tgttttttt gtggttttatc      60
gtgccgttct ggtttgctgt gctcgtcaac gccgacagca acaacagctc ccattttcag    120
tcgatttata acttgacgct atgtgagctg aatggcacag attggctggc taaccatttt    180
gattgggcag tggaggcttt tgttatcttt cccgcgttga ctcacattgt ttcctatggt    240
gcacttacca ccagccattt ccttgacaca gttggtctgg ttactgtgtc caccgccggg    300
tttcgtcaca agcggtatgt cttgagtagc atctacgcgg tctgtgccct ggctgcgttg    360
atttgcttcg tcatcagatt tgcgaagaac tgcatgtcct ggcgctactc atgtaccaga    420
tataccaact tccttctaga tactaagggc aggctctatc ggtggcggtc gcctgttatc    480
atagagaaag ggggtaaggt tgaggtcgga ggccacctga tcgacctcaa aagagttgtg    540
cttgatggtt ccgtggcaac tcctttaacc agagtttcag ctgaacaatg gggtcgtccc    600
tag                                                                  603
```

PORCINE REPRODUCTIVE AND RESPIRATORY SYNDROME VIRUS STRAINS AND COMPOSITIONS

PRIORITY CLAIM TO RELATED PATENT APPLICATIONS

This patent claims priority under 35 U.S.C. §371 as a national phase of International Patent Application No. PCT/US2005/040366 (filed Nov. 8, 2005; and published on May 26, 2006 as International Publication No. WO 2006/055331), which, in turn, claims priority to U.S. Provisional Patent Application Nos. 60/629,873 (filed Nov. 19, 2004) and 60/674,002 (filed Apr. 21, 2005). The entire text of each of the above-referenced patent applications is hereby incorporated by referenced into this patent.

REFERENCE TO SEQUENCE LISTING

The material saved as "text document" under the file name "SubstituteSequenceListing" created on May 21, 2009 is hereby incorporated by reference.

FIELD OF THE INVENTION

This invention relates to two attenuated strains of porcine reproductive and respiratory syndrome virus (PRRSV) and immunogenic compositions comprising one or more strains of attenuated porcine reproductive and respiratory syndrome virus (PRRSV).

BACKGROUND OF THE INVENTION

PRRS was recognized for the first time in the United States in 1987. It quickly spread throughout all of the major swine producing areas of North America. It next appeared in Europe, and today PRRSV has almost worldwide distribution. Many swine producers, government officials, and veterinarians believe that PRRS is currently one of the most serious economic threats faced by the swine industries worldwide.

As its name implies, PRRS is characterized clinically by its ability to cause reproductive failure in pregnant females, especially when initially infected late in gestation, and respiratory tract illness in pigs of all ages, but most common and severe in young pigs. A PRRSV infection is also thought to potentiate the effects of other swine pathogens. On the basis of retrospective serological studies, it also has become evident that many infections of swine with PRRSV are either subclinical or result in less obvious clinical signs. Therefore, the PRRSV often gains access to a herd and spreads extensively before its presence is first detected.

The virus can persist in an infected host for at least several months. Such "carriers" perpetuate the infection and make control of the disease extremely difficult. As a consequence, the most effective means for reducing the economic impact of PRRSV is to vaccinate (immunize) potentially susceptible pigs before they are exposed to virulent field virus.

Attenuated vaccines, (manufactured by Boehingher Ingelheim) prepared from single strains of PRRSV, are commercially available. One is licensed for use in pigs between 3 and 18 weeks of age for the prevention of respiratory tract illness (Gorcyca et al., 1995). One is licensed for pre-breeding.

Another attenuated vaccine has been described for the prevention of reproductive failure (Hesse et al., 1996). It is prepared from a single strain of PRRSV and has only been tested against a single strain of PRRSV. The challenge strain is described as heterologous on the basis of the anamnestic response of vaccinated gilts following challenge; however, no other evidence has been presented to establish that the two strains, i.e., the one used for the vaccine and the one used for challenge of immunity, are genetically or antigenically different.

There are two known major serotypes of PRRSV (Done et al., 1996). One (prototype Lelystad) is representative of at least most strains that have been isolated in Western Europe. The other (prototype ATCC 2332) is representative of at least most strains isolated in North America and Asia. There also are antigenic variants within prototypes (Meng et al., 1995), and base sequence differences among strains isolated in North America have allowed for their differentiation (Wesley et al., 1996).

SUMMARY OF THE INVENTION

An object of the present invention is to provide an immunogenic composition which protects a pig against clinical disease caused by PRRSV. The immunogenic compositions were derived from two strains of PRRSV that were isolated in the United States from pigs affected with PRRSV.

Another object of the invention is to provide attenuated strains of PRRSV that would be useful in a polyvalent vaccine against PRRS.

The present invention is not limited to the expressed objects above, as other objects and advantages of this invention will become readily apparent from the ensuing description.

Deposit of Biological Material

Attenuated strains PP5 and LC13 were deposited on Nov. 4, 2004 under the terms of the Budapest Treaty at the American Type Culture Collection in Manassas, Va. and have been assigned Accession Nos. ATCC PTA-6282 and ATCC PTA-6281, respectively. Pursuant to 37 C.F.R. §1.808, the biological material is made under two conditions. First, access to the deposit will be made available during pendency of the patent application making reference to the deposit to one determined by the Commissioner to be entitled thereto under 37 C.F.R. §1.14 and 35 U.S.C. §122; and secondly with one exception, that restrictions imposed by the depositor on the availability to the public of the deposited material be irrevocably removed upon the granting of the patent.

DETAILED DESCRIPTION OF THE INVENTION

"Immunogenic composition" is defined herein in its broad sense to refer to any type of biological agent in an administratable form capable of stimulating an immune response in an animal. For purposes of this invention, the immunogenic composition may comprise as the viral agent either the virus itself or an immunogenic (antigenic) component of the virus.

The immunogenic composition of the invention was prepared from any one or more of the two attenuated strains of PRRSV: PP5 and LC13. Each strain was individually tested for safety and ability to induce and immune response, and it is contemplated that a polyvalent vaccine comprised of the two strains would be at least as safe and effective as each monovalent composition and might provide even broader immunity to virulent field strains of PRRSV.

Two strains of PRRSV (strains PP5 and LC13) were selected for development as immunogenic compositions and vaccines.

PRRSV Strain PP5

A virulent isolate of PRRS virus was obtained from tissue samples from a diseased pig. A tissue homogenate from the diseased pig was inoculated onto primary alveolar macrophages and the presence of virus was detected by cytopathic effects on inoculated but not control cultures. The isolated virus was subsequently demonstrated by reactivity with monoclonal antibodies specific for the PRRS virus by indirect immunofluorescence. 96-well plates of confluent Marc145 cells were fixed with 80% acetone for 10 minutes at 2 days after infection with the virus. Monolayers were then incubated with SDOW17 or VO17 monoclonal antibodies. Following washing, monoclonal antibody reactivity with each virus was detected by incubation with fluorescein isothiocyanate conjugated anti-mouse IgG followed by washing and examination for fluorescence by microscopy. Positive fluorescence was noted with both monoclonal antibodies for the PP5 virus. The PP5 virus was attenuated by serial passage in tissue culture. The virus was initially passed by inoculation of primary swine alveolar macrophage (SAM) cultures (for the first passage) and then by serial passage on Marc145 cells for a total of 81 passages. During this process, virus clones were isolated by plaque purification and characterized for phenotypic properties. The immunogenic composition clone PP5 was selected for impaired growth on swine alveolar macrophages and lack of disease induction in piglets and pregnant sows. The PP5 was expanded on Marc145 cells and frozen as a master seed virus.

PP5 can be differentiated from other isolated attenuated PRRSV strains by the ORF5 region of its sequence. The PP5 ORF5 sequence is represented by SEQ ID No.:1.

PRRSV Strain LC13

A virulent isolate of PRRS virus was obtained from tissue samples from a diseased pig. A tissue homogenate from a diseased pig was inoculated onto primary alveolar macrophages and the presence of virus detected by cytopathic effects on inoculated but not control cultures. The isolated virus was subsequently demonstrated to be reactive with monoclonal antibodies specific for the PRRS virus by indirect immunofluorescence. 96-well plates of confluent Marc145 cells were fixed with 80% acetone for 10 minutes at 2 days after infection with the virus. Monolayers were then incubated with SDOW17 or VO17 monoclonal antibodies. Following washing, monoclonal antibody reactivity with each virus was detected by incubation with fluorescein isothiocyanate conjugated anti-mouse IgG followed by washing and examination for fluorescence by microscopy. Positive fluorescence was noted with both monoclonal antibodies for the LC13 virus. The LC13 virus was attenuated by serial passage in tissue culture. The virus was initially isolated in primary swine alveolar macrophage cultures and then was serially passaged on Marc145 cells for a total of 67 passages. During this process, virus clones were isolated by plaque purification and characterized for phenotypic properties. The immunogenic composition clone (LC13) was selected for impaired growth on swine alveolar macrophages and lack of disease induction in piglets and pregnant sows. The LC13 was expanded on Marc145 cells and frozen as a master seed virus.

LC13 can be differentiated from other isolated attenuated PRRSV strains by the ORF5 region of its sequence. The LC13 ORF5 sequence is represented by SEQ ID No.:2.

The composition virus or viruses were prepared for administration by formulation in an effective immunization dosage with a pharmaceutically acceptable carrier or diluent, such as physiological saline or tissue culture medium. The expression "effective amount" is defined as being that amount which will induce immunity in a pig against challenge by a virulent strain of PRRSV. Determination of actual dosage amounts would be fully within the skill of a person in the art. Based on the examples given below, it is contemplated that one embodiment is a single dosage of approximately $10^{4.5}$ $TCID_{50}$/ml.

The compositions can be administered orally, oronasally or by injection. Appropriate adjuvants as known in the art may be included in the composition formulation. As previously mentioned, the subject immunogenic compositions or vaccines may be used individually, or they may be combined together in any combination in the formulation of a polyvalent composition.

The following examples are used to illustrate successful attainment of the objectives of the invention. None are intended to limit its scope of applicability.

EXAMPLES

An immunogenic composition was prepared using MARC145 as the substrate (however alternate cell lines that support the growth of PRRS virus such as MA104 cells can also be used). MARC145 cells were grown to confluency in suitable tissue culture vessels (i.e. 850 cm$^2$ roller bottles) using Eagle's minimum essential media (EMEM) containing 5 to 10% fetal bovine serum, 2 mM L-glutamine, and antibiotics (such as 30 µg/ml gentamicin). Alternate tissue culture media that can support the growth of MARC145 cells such as Dulbecco's modified essential media [DMEM], Medium 199, or others can also be used. Confluent monolayers of MARC145 cells were inoculated with PP5 or LC13 at a multiplicity of infection (MOI) of 1:10 (MOI's in the range of 1:5 to 1:1000 can be used). Following incubation for three to five days at 37° C., culture supernatant fluids were harvested by decanting.

Virus fluids were titered by making serial dilutions in EMEM supplemented as above and inoculation of 0.2 ml per well into at least four replicate wells of confluent MARC145 or MA104 cells in a 96-well tissue culture plate. Cultures were incubated for five days at 37° C., 3-5% $CO_2$ in a humidified chamber and observed for cytopathic effects. Titers (50% endpoints) were calculated according to the methods of Spearman and Karber.

For the preparation of a killed immunogenic composition or killed vaccine formulation, virus fluids were incubated with a chemical inactivation agent such as formaldehyde, glutaraldehyde, binary ethyleneimine, or beta-propiolactone. Virus fluids were then stored at 4° C. until formulated into immunogenic composition. Immunogenic composition was prepared by mixing virus fluids (containing $10^5$ to $10^9$ $TCID_{50}$ of virus; based on pre-inactivation titers) with a physiologically acceptable diluent (such as EMEM, Hank's Balanced Salt Solution®, phosphate buffered saline) and an immune-stimulating adjuvant (such as mineral oil, vegetable oil, aluminum hydroxide, saponin, non-ionic detergents, squalene, or other compounds known in the art, used alone or in combination). An immunogenic composition dose was typically between 1 and 5 ml.

For a live immunogenic composition or live vaccine formulation, virus fluids (attenuated virus) are stored frozen at −50° C. or colder until use. Virus fluids (typically containing $10^{6.0}$ $TCID_{50}$/dose but within the range of $10^{3.0}$ and $10^{7.0}$ $TCID_{50}$/dose) are diluted with a physiologically suitable diluent (such as EMEM, Hank's Balanced Salt Solution®, phosphate buffered saline) and a physiologically suitable mixture of compounds designed to stabilize the virus. Compounds known in the art that can be used alone or in combination to stabilize viruses include sucrose, lactose, N-Z amine, glutathione, neopeptone, gelatin, dextran, and tryptone. Vaccine is stored frozen (−50° C. or colder) or lyophilized with storage at 4° C. until use. The immunogenic composition or vaccine typically has a dose size of 2 ml (range of 1 to 5 ml).

For prophylaxis against PRRS-induced disease, swine are vaccinated with live or killed immunogenic composition by intradermal, intramuscular, subcutaneous, intranasal, or oral administration of one dose of vaccine. A booster vaccination may be administered two to four weeks after the initial immunization. For the prevention of PRRS associated disease, the vaccination regimen is typically initiated up to 6 weeks prior to breeding and can be given as late a one week after breeding. For the prevention of respiratory disease in piglets, vaccination may be given as early as 3 weeks of age.

Examples of Strain Attenuation and their Ability to Induce Immune Response

PP5 Experiment

PRRS seronegative sows at 85 days gestation were inoculated intranasally (3 ml/nare) with the master seed vaccine strains PP5 ($10^{4.5}$ TCID$_{50}$/ml). All sows farrowed at their expected time.

Table 1 provides the results for the PP5 PRRS virus strain experiment. The first group PP5-WT is the wild type virus or virulent/disease control. Group PP5-MSV is the master seed virus of the attenuated PP5 strain. PP5-BP represents the fifth backpassage (pig passage) from PP5-MSV to see if the any reversion to wild type virus takes place.

The results from the PP5 experiment are summarized in Table 2. PP5-WT caused parturition mortality of 69% compared to PP5-MSV and PP5-BP only having caused 16% parturition mortality to 19% parturition mortality, respectively.

TABLE 1

PP5

| Group | Sow # | Elisa Antibody | % Mortality @ Birth |
|---|---|---|---|
| PP5-WT | 40 | NT | 100% |
| PP5-WT | 165 | 0.9 | 85% |
| PP5-WT | 313 | 1.3 | 67% |
| PP5-WT | 1138 | 1.2 | 25% |
| PP5-WT | 1156 | 1.2 | 45% |
| PP5-WT Totals | | | 69% |
| PP5-MSV | 1344 | 0.511 | 20% |
| PP5-MSV | 1347 | 0.002 | 0% |
| PP5-MSV | 1348 | 1.005 | 40% |
| PP5-MSV | 1350 | 1.151 | 15% |
| PP5-MSV | 1353 | 0.899 | 0% |
| PP5-MSV | 1355 | 1.188 | 13% |
| PP5-MSV Totals | | | 16% |
| PP5-BP | 1345 | 0.932 | 38% |
| PP5-BP | 1346 | 0.56 | 13% |
| PP5-BP | 1349 | 0.515 | 33% |
| PP5-BP | 1351 | 0.569 | 0% |
| PP5-BP | 1352 | 1.174 | 27% |
| PP5-BP | 1354 | 0.624 | 0% |
| PP5-BP Totals | | | 19% |

TABLE 2

Summary of PP5

| | % Mortality @ Birth | |
|---|---|---|
| Wild Type Virus | 69% | PP5-WT |
| Master Seed Virus | 16% | PP5-MSV |
| Back Passage Virus | 19% | PP5-BP |

LC13 Experiment

PRRS seronegative sows at 85 days gestation were inoculated intranasally (3 ml/nare) with the master seed vaccine strain LC13 ($10^{4.5}$ TCID$_{50}$/ml). All sows farrowed at their expected time.

Table 3 provides the results for the LC13 PRRS virus strain experiment. The first group LC13-WT is the wild type virus or disease/virulent control. Group LC13-MSV is the master seed virus of the attenuated LC13 strain. LC13-BP represents the fifth backpassage (pig passage) from LC13-MSV to see if the any reversion to wild type virus takes place.

The results from the LC13 experiment are summarized in Table 4. LC-WT caused parturition mortality in 86% of the piglets, whereas LC13-MSV and LC13-BP only caused 12% parturition mortality to parturition 15% mortality, respectively.

TABLE 3

LC13

| Group | Sow # | Elisa Antibody | % Mortality @ Birth |
|---|---|---|---|
| LC13-WT | 187 | 1.3 | 75% |
| LC13-WT | 309 | NT | 100% |
| LC13-WT | 518 | 0.8 | 100% |
| LC13-WT | 858 | 1.2 | 88% |
| LC13-WT | 1041 | 1.2 | 56% |
| LC13-WT Totals | | | 86% |
| LC13-MSV | 843 | 1.0 | 0% |
| LC13-MSV | 845 | 0.7 | 8% |
| LC13-MSV | 846 | 0.0 | 0% |
| LC13-MSV | 848 | 1.1 | 25% |
| LC13-MSV | 850 | 1.0 | 11% |
| LC13-MSV Totals | | | 12% |
| LC13-BP | 844 | <0.1 | 0% |
| LC13-BP | 847 | <0.1 | 31% |
| LC13-BP | 849 | <0.1 | 10% |
| LC13-BP | 851 | <0.1 | 11% |
| LC13-BP | 853 | <0.1 | 0% |
| LC13-BP Totals | | | 13% |

TABLE 4

Summary of LC13

| | % Mortality ® Birth | |
|---|---|---|
| Wild Type Virus | 86% | LC-13-WT |
| Master Seed Virus | 12% | LC13-MSV |
| Back Passage Virus | 13% | LC13-BP |

The enzyme-linked immunosorbent assay (Elisa) antibody data found in Tables 1 and 3 represents the results from an Elisa antibody assay on the saws. ELISA is the most commonly used test for detecting antibodies against PRRS. The HerdChek PRRS ELISA manufactured by IDEXX Laboratories Inc. is for detection of anti-PRRSV nucleocapsid (N) protein antibodies from swine serum or plasma. Test results were determined based on the Sample/Positive (S/P) values: positive=S/P ratio>0.4, negative=S/P ratio<0.4. As the results show in Table 1 and 3, both LC13-MSV and PP5-MSV raised antibodies for PRRS. This data generated provides evidence of an immunogenic composition.

The data presented in this application clearly demonstrates that the attenuated PRRS virus strains PP5 and LC13 are both safe and induce an immune response.

I claim:

1. An immunogenic composition for inducing an immune response against a disease caused by porcine reproductive and respiratory syndrome, comprising:
   an effective amount of an attenuated PRRS virus selected from the group consisting of attenuated PRRS virus ATCC PTA-6281, attenuated PRRS virus ATCC PTA-6282 and combinations thereof; and
   a pharmaceutically acceptable carrier or diluent.

2. The immunogenic composition of claim 1, wherein said virus is attenuated PRRS virus ATCC PTA-6281.

3. The immunogenic composition of claim 1, wherein said virus is attenuated PRRS virus ATCC PTA-6282.

4. A polyvalent immunogenic composition for inducing an immune response against a disease caused by porcine reproductive and respiratory syndrome, comprising:
   an effective amount of PRRS virus ATCC PTA-6281 and PRRS virus ATCC PTA-6282.

5. The immunogenic composition of claim 1, further comprising an adjuvant.

6. An attenuated porcine reproductive and respiratory syndrome virus PP5 as represented by ATCC deposited NO. PTA-6282.

7. An attenuated porcine reproductive and respiratory syndrome virus LC13 as represented by ATCC deposited NO. PTA-6281.

8. A method for protecting a swine against porcine reproductive and respiratory syndrome, comprising:
   inoculating said swine with an effective amount of an attenuated PRRS virus selected from the group consisting of attenuated PRRS virus ATCC PTA-6281, attenuated PRRS virus ATCC PTA-6282 and combinations thereof, wherein said attenuated PRRS virus is formulated in a pharmaceutically acceptable carrier or diluent.

9. The method of claim 8, wherein said virus is attenuated PRRS virus ATCC PTA-6281.

10. The method of claim 8, wherein said virus is attenuated PRRS virus ATCC PTA-6282.

11. The method of claim 9, wherein said formulation further comprises an adjuvant.

12. An attenuated porcine respiratory and reproductive syndrome virus ORF5 comprising the sequence of SEQ ID NO:1 or SEQ ID NO:2.

\* \* \* \* \*